US008623842B2

(12) United States Patent
Roberts et al.

(10) Patent No.: US 8,623,842 B2
(45) Date of Patent: Jan. 7, 2014

(54) HEMOSTATIC AGENT AND METHOD

(75) Inventors: Keith A. Roberts, White Bear Lake, MN (US); John Henry Burban, Lake Elmo, MN (US); Majid Zia, White Bear Township, MN (US); Michael R. Spearman, The Woodlands, TX (US)

(73) Assignee: Hemostasis, LLC, St. Paul, MN (US)

( * ) Notice: Subject to any disclaimer, the term of this patent is extended or adjusted under 35 U.S.C. 154(b) by 1415 days.

(21) Appl. No.: 11/861,719

(22) Filed: Sep. 26, 2007

(65) Prior Publication Data

US 2008/0076722 A1 Mar. 27, 2008

Related U.S. Application Data

(60) Provisional application No. 60/847,629, filed on Sep. 27, 2006.

(51) Int. Cl.
*A61K 31/715* (2006.01)

(52) U.S. Cl.
USPC .......................................................... 514/60

(58) Field of Classification Search
USPC .......................................................... 514/60
See application file for complete search history.

(56) References Cited

U.S. PATENT DOCUMENTS

| | | | |
|---|---|---|---|
| 2,423,475 A | 7/1947 | Bice et al. ...................... 128/270 |
| 2,465,357 A | 3/1949 | Correll .......................... 106/122 |
| 2,507,244 A | 5/1950 | Correll .......................... 260/117 |
| 2,558,395 A | 6/1951 | Studer ........................... 424/423 |
| 2,602,042 A | 7/1952 | Abbott ............................ 167/84 |
| 3,005,457 A | 10/1961 | Millman ........................ 128/296 |
| 3,122,479 A | 2/1964 | Smith ............................. 167/84 |
| 3,208,994 A | 9/1965 | Flodin .......................... 260/209 |
| 3,328,250 A | 6/1967 | Mentzer ......................... 167/65 |
| 3,810,473 A | 5/1974 | Cruz, Jr. et al. ............... 128/334 |
| 3,813,466 A | 5/1974 | Anderson ....................... 424/28 |
| 4,002,173 A | 1/1977 | Manning et al. .............. 128/296 |
| 4,124,705 A | 11/1978 | Rothman et al. .............. 424/180 |
| 4,126,669 A | 11/1978 | Rothman et al. ................ 424/1 |
| 4,144,040 A | 3/1979 | Claes et al. ...................... 55/97 |
| 4,215,200 A | 7/1980 | Miyata et al. ................. 435/273 |
| 4,225,580 A | 9/1980 | Rothman et al. .............. 424/87 |
| 4,292,972 A | 10/1981 | Pawelchak et al. ........... 128/296 |
| 4,394,373 A | 7/1983 | Malette et al. .................. 424/95 |
| 4,439,420 A | 3/1984 | Mattei et al. ................. 424/78.38 |
| 4,459,139 A | 7/1984 | vonReis et al. ................ 55/189 |
| 4,537,767 A | 8/1985 | Rothman et al. .............. 424/87 |
| 4,640,834 A | 2/1987 | Eibl et al. ....................... 424/94 |
| 4,822,349 A | 4/1989 | Hursey et al. ................. 604/367 |
| 5,089,606 A | 2/1992 | Cole et al. ..................... 536/54 |
| 5,199,944 A | 4/1993 | Cosmescu ...................... 604/26 |
| 5,290,237 A | 3/1994 | Verkaart ........................ 604/126 |
| 5,336,169 A | 8/1994 | Divilio et al. ................. 604/22 |
| 5,409,703 A | 4/1995 | McAnalley et al. .......... 424/435 |
| 5,578,000 A | 11/1996 | Greff et al. .................... 604/22 |
| 5,585,007 A | 12/1996 | Antanavich et al. .......... 210/782 |
| 5,688,256 A | 11/1997 | Surratt et al. ................. 604/355 |
| 5,707,972 A | 1/1998 | Shimizu ......................... 514/54 |
| 5,722,962 A | 3/1998 | Garcia .......................... 604/264 |
| 5,770,705 A | 6/1998 | Shanbrom | |
| 5,836,970 A | 11/1998 | Pandit .......................... 606/213 |
| 5,840,777 A | 11/1998 | Eagles et al. .................. 521/82 |
| 5,851,461 A | 12/1998 | Bakis et al. ................... 264/50 |
| 6,060,461 A * | 5/2000 | Drake ............................ 514/54 |
| 6,110,259 A | 8/2000 | Schultz et al. ................. 96/273 |
| 6,576,033 B1 | 6/2003 | Booth ........................... 55/485 |
| 6,589,316 B1 | 7/2003 | Schultz et al. ................. 95/273 |
| 6,592,543 B1 | 7/2003 | Wortrich et al. ............... 604/35 |
| 6,638,918 B2 | 10/2003 | Davison et al. ................ 514/55 |
| 6,746,504 B2 | 6/2004 | Booth ........................... 55/485 |
| 6,992,233 B2 | 1/2006 | Drake et al. ................... 602/48 |
| 7,070,722 B1 | 7/2006 | Gilchrist et al. .............. 264/50 |
| 7,101,862 B2 | 9/2006 | Cochrum et al. .............. 514/54 |
| 7,371,043 B2 | 5/2008 | McCarthy et al. ............ 424/445 |
| 2002/0131933 A1 | 9/2002 | Delmotte ..................... 424/1.11 |
| 2003/0073663 A1 | 4/2003 | Wiseman et al. .............. 514/54 |
| 2003/0183082 A1 | 10/2003 | Schultz et al. ................. 95/273 |
| 2004/0243043 A1 | 12/2004 | McCarthy et al. ............ 602/46 |
| 2005/0038369 A1 | 2/2005 | Gregory et al. ................ 602/48 |
| 2005/0137512 A1 | 6/2005 | Campbell et al. .............. 602/41 |
| 2005/0147656 A1 | 7/2005 | McCarthy et al. ............ 424/445 |
| 2007/0066924 A1 | 3/2007 | Hopman et al. ................ 602/48 |
| 2007/0082023 A1 | 4/2007 | Hopman et al. .............. 424/426 |
| 2007/0148215 A1 | 6/2007 | Teslenko et al. .............. 424/445 |
| 2008/0082084 A1 | 4/2008 | Roberts et al. | |
| 2009/0062233 A1 | 3/2009 | Ji et al. ........................... 514/60 |
| 2010/0291055 A1 | 11/2010 | Athanasiadis et al. ....... 424/94.1 |

FOREIGN PATENT DOCUMENTS

WO    WO 2008/150246 A1    12/2008    ........... A61K 36/185

OTHER PUBLICATIONS

Murat, F.-J.L., Ereth, M.H., Dong, Y., Piedra, M.P., Gettman, M.T. (2004) Evaluation of Microporous Polysaccharide hemospheres as a Novel Hemostatic Agent in Open Partial Nephrectomy: Favorable Experimental Results in the Porcine Model. The Journal of Urology, vol. 172, p. 1119-1122.*

Niba, L.L. (2006) "Carbohydrates: Starch" in Handbook of Food Science, Technology, and Engineering, vol. 1. Edited by Y.H. Hui, published by CRC Press Taylor & Francis, p. 3-1 to 3-17.*

"Vitamin K" from the Vitamin & Herb University [online]. [Retrieved on Sep. 4, 2010]. Retrieved from the internet at http://www.vitaminherbuniversity.com/topic.asp?categoryid=1&topicid=1011, published Sep. 25, 2003.*

Mitolo, J.J. (2006) "Starch Selection and Interaction in Foods" in Ingredient Interactions: Effects on Food Quality. Second Edition. Edited by Andrew McPherson and Anilkumar G. Gaonkar. Published by CRC Press, p. 139-166. Release date: Dec. 20, 2005.*

(Continued)

*Primary Examiner* — Elli Peselev
(74) *Attorney, Agent, or Firm* — Baker Botts L.L.P.

(57) ABSTRACT

One aspect of the invention is a method of treating a wound to clot blood. A sponge material is applied to the wound. The sponge comprises a starch having hemostatic properties and at least one binding agent. The sponge may further comprise a porous, flexible material.

13 Claims, 2 Drawing Sheets

(56) References Cited

OTHER PUBLICATIONS

Food Industries Manual (1997) Edited by M.D. Ranke, R.C. Kill and C. Baker. Published by Blackie Academic and Professional, London, UK, p. 488-489.*

International Search Report, mailing date Feb. 15, 2008, for International Application No. PCT/TR2007/00129, filed Feb. 4, 2008 (3 pgs), Feb. 4, 2008.

Lloyd, et al., *System and Method to Vent Gas from a Body Cavity*, U.S. Appl. No. 12/041,233, filed Mar. 3, 2008.

Roberts, et al., *Hemostatic Sponge and Method of Manufacture*, U.S. Appl. No. 61/068,226, filed Mar. 4, 2008.

Bhaskara Jasti, et al.; Business Briefing: Pharmatech; *Drug Delivery Polymers: Recent Advances in Mucoadhesive Drug Delivery Systems*; 3 pages, 2003.

Eric M. Acheson, et al.; The Journal of TRAUMA200 Injury, Infection, and Critical Care; *Comparison of Hemorrhage Control Agents Applied to Lethal Extremity Arterial Hemorrhages in Swine*; vol. 59, No. 4; pp. 865-875. Oct. 2005.

Ott, Douglas E., *Smoke Production and Smoke Reduction in Endoscopic Surgery: Preliminary Report*, End. Surg; 1993, No. 4, vol. 1: 230-232 (4 pages), Aug. 1993.

Ott, Douglas E., *Carboxyhemoglobinemia Due to Peritoneal Smoke Absorption from Laser Tissue Combustion at Laparoscopy*, Journal of Clinical Laser Medicine & Surgery, vol. 16, No. 6, 1998, pp. 309-315 (7 pages).

PCT, Notification of Transmittal of the International Search Report and the Written Opinion of the International Searching Authority, or the Declaration, International Application No. PCT/US2009/035386, Int'l filing date Feb. 27, 2009, and PCT International Search Report, 13 pgs, Date Mailed May 31, 2010.

Keith A. Roberts, *Hemostatic Sponge with Enzyme and Method of Manufacture*, U.S. Appl. No. 61/238,754, filed Sep. 1, 2009.

USPTO; Office Action; U.S. Appl. No. 12/390,947, filed Feb. 23, 2009, in the name of Roberts, ( 6 pgs ), Notification Date Dec. 08, 2010.

Keith A. Roberts, *Hemostatic Sponge with Enzyme and Method of Manufacture*, U.S. Appl. No. 12/853,083, filed Aug. 9, 2010 (28 pgs).

USPTO; Non-Final Office Action; U.S. Appl. No. 12/390,947, filed Feb. 23, 2009, in the name of Keith A. Roberts, ( 23 pgs ), Notification Date Mar. 14, 2011.

USPTP; Non-Final Office Action; U.S. Appl. No. 12/853,083, filed Aug. 9, 2010; in the name of Keith A. Roberts , (26 pgs) Notification Date Mar. 24, 2011.

Akira Ito, et al., Die Angewandte Makromolekulare Chemie 248 (1997), pp. 85-94, "Permeability of $CO_2$ through chitosan membrane swollen by water vapor in feed gas", Dept. of Material and Chemical Engineering, Niigata Univ., Japan (10 pgs).

Fwu-Long Mi et al., Biomaterials 22 (2001) pp. 165-173; "Fabrication and characterization of a sponge-like asymmetric chitosan membrane as a wound dressing", Republic of China (9 pgs).

USPTO; Final Office Action; U.S. Appl. No. 12/853,083, filed Aug. 9, 2010, in the name of Keith A. Roberts, ( 34 pgs.) Notification Date Aug. 12, 2011.

Roberts et al., U.S. Appl. No. 12/390,947, "Response Pursuant to 37 C.F.R. §1.111", (12 pgs.), filed Jun. 3, 2011.

Roberts et al., U.S. Appl. No. 12/853,083, "Response Pursuant to 37 C.F.R. §1.111", (16 pgs.), filed Jun. 20, 2011.

Park, S.-I., et al. , "Functional Properties of Antimicrobial Lysozyme—Chitosan Composite Films", 2004 Institute of Food Technologists, vol. 69, Nr. 8, 2004, Journal of Food Science, Published on Web Sep. 29, 2004; pp. M215-M221.

"Absorbable Hemostatic Particles Microporous Polysaccharide Hemosphere (MPH®) Technology", medafor Hemostatic Polymer Technologies, LIT-0057 Rev E Oct. 2008 (2 pgs.) http://www.medaforinc.com/documents/products/AristaAH.pdf.

J. Fannon, J. Gray, N. Gunaway, K. Huber, J. BeMiller, "Heterogeneity of Starch Granules and the Effect of Granule Channelization on Starch Modification", Whistler Center for Carbohydrate Research, Purdue University, revised Nov. 28, 2003, Paper presented in Symposium on Modified Starches, American Chemical Society, New Orleans, Louisiana (8 pgs.), Mar. 23-27, 2003.

C. Tschan M. Nie, E. Schwandt, J. Oertel, "Safety and Efficacy of Microporous Polysaccharide Hemospheres in Neurosurgry", Neurosurgery . 69 Operative Neurosurgery, 1:ons49-ons63, Sep. 2011. doi: 10.1227/NEU.06-l3e3182155a51, http://stage-mobile.journals.1ww.com/neurosurgery/$_{13}$ layouts/oaks.journals.mobile/articlevi . . . (16 pgs), May 4, 2011.

Roberts et al., U.S. Appl. No. 12/390,947, "Appeal Brief", (39 pgs.), filed Nov. 3, 2011.

"Examiners Answer to Appeal Brief", Roberts et al., U.S. Appl. No. 12/390,947, (36 pgs.), Notification Date Feb. 2, 2012.

USPTO; Final Office Action; U.S. Appl. No. 12/390,947, filed Feb. 23, 2009, in the name of Keith A. Roberts, ( 28 pgs ), Notification Date Jun. 20, 2011.

Roberts et al., U.S. Appl. No. 12/390,947, RCE, "Response Pursuant to 37 C.F.R. §1.114", (9 pgs.), filed Mar. 28, 2012.

J. Fannon, R. Hauber, J. BeMiller, "Surface Pores of Starch Granules", 1992 American Association of Cereal Chemists, Inc., vol. 69, No. 3, 1992 (5 pgs.).

"About Medafor", medafor Hemostatic Polymer Technologies, http://www.medaforinc.com/about.aspx, (3 pgs.), Printed on Oct. 3, 2011.

J. Fannon, J. Gray, N. Gunaway, K. Huber, J. BeMiller, "Heterogeneity of Starch Granules and the Effect of Granule Channelization on Starch Modification", Whistler Center for Carbohydrate Research, Purdue University, recieved Jun. 25, 2003/revised Nov. 28, 2003, Paper presented in Symposium on Modified Starches, American, Chemical Society, New Orleans, Louisiana (8 pgs.), Mar. 23-27, 2003.

B. Lindberg, K. Lote, H. Teder, "Biodegradable Starch Microspheres—A new Medical Tool", Microspheres and Drug Therapy, Pharmaceutical, Immunological and Medical Aspects, Elsevier Science Publishers B.V. (36 pgs.), 1984.

Magle Life Sciences; Magle AB—Our Products, "Products", http://www.magle.se/our_products;jsessionid=033C6D6E207028CB7F1806B2795DBCD6 (2 pgs), Printed on Nov. 1. 2011.

Tina B. Merritt DVM, "Help! My Bird is Bleeding", Winged Wisdom Pet Bird Magazine, Ezine, Nov. 1997 Magazine, Article V, http://www.birdsnways.com/wisdom/ww17ev.htm (2 pgs), Printed on Nov. 1, 2011.

C. Tschan M. Nie, E. Schwandt, J. Oertel, "Safety and Efficacy of Microporous Polysaccharide Hemospheres in Neurosurgery", Neurosurgery. 69 Operative Neurosurgery, 1:ons49-ons63, Sep. 2011. doi: 10.1227/NEU/06-l3e3182155a51, http://stage-mobile.journals.1ww.com/neurosurgery/_layouts/oaks.journals.mobile/articlevi . . . (16 pgs), May 4, 2011.

\* cited by examiner

HEMOSTATIC AGENT AND METHOD

CROSS REFERENCE TO RELATED APPLICATIONS

This application claims the benefit of U.S. Provisional Application Ser. No. 60/847,629, filed Sep. 27, 2006, entitled "Hemostatic Agent and Method", the disclosure of which (including draft claims) is incorporated herein by reference in its entirety as if fully set forth herein.

TECHNICAL FIELD OF THE INVENTION

This invention relates generally to hemostatic agents and more particularly to a hemostatic agent, a method of making hemostatic agents, and a method of treatment.

BACKGROUND OF THE INVENTION

Human blood clots to deter bleeding from wounds. Sometimes, however, it is desirable to stop bleeding and facilitate clotting faster than the human body would achieve clotting on its own. To clot blood more quickly, medical personnel will sometimes use hemostatic agents. A hemostatic agent may promote clotting and thereby stop or control bleeding. Some individuals may use hemostatic agents to promote more rapid clotting of cuts or other bleeding wounds.

SUMMARY OF THE INVENTION

One aspect of the invention is a method of treating a wound to clot blood. A sponge material is applied to the wound. The sponge comprises a starch having hemostatic properties and at least one binding agent. The sponge may further comprise a porous, flexible material.

The invention has several important technical advantages. Embodiments of the invention may have none, some, or all of these advantages without departing from the scope of the invention. Many types of hemostatic agents come in powder form. Powder can be an inconvenient form of delivery as it is difficult to handle. In addition, powder can be difficult to apply to various areas of the body such as the nose, the gums during oral surgery, or the back. In some embodiments, the invention allows the user to treat a wound more easily in such places. The invention may employ polysaccharides as hemostatic agents. Most polysaccharides are nontoxic to the human body and believed to be nontoxic to most animals that may be treated with a hemostatic sponge. The inventors have discovered that a hemostatic sponge with significant flexibility can be made using the techniques described herein. Thus, some embodiments may include a hemostatic sponge that can be manipulated in various ways without cracking or tearing. Some embodiments may use modified pregelatinized potato starch as a hemostatic agent. This agent may be easily absorbed by the body and may promote stable clotting because it is a long branch molecule. It may also promote rapid clotting.

BRIEF DESCRIPTION OF THE DRAWINGS

For a more complete understanding of the present invention and the advantages thereof, reference is now made to the following descriptions taken in conjunction with the accompanying drawings in which.

DETAILED DESCRIPTION OF THE INVENTION

Figure 1:
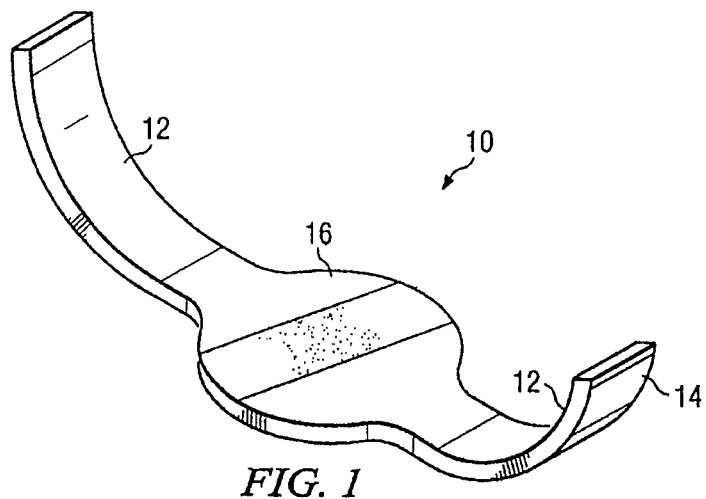
FIG. 1 illustrates one example embodiment of a bandage with a hemostatic agent in accordance with one aspect of the invention.

The preferred embodiment of the invention and its advantages are best understood by referring to FIGS. 1-5 of the drawings, like numerals being used for like and corresponding parts of the drawings. The embodiment described herein is only one embodiment of the invention and various substitutions and alterations can be made without departing from the scope of the invention.

One aspect of the invention is a sponge comprising a hemostatic agent. In some embodiments, the sponge comprises a polysaccharide hemostatic agent. Example polysaccharide hemostatic agents may include natural, plant-based, polysaccharides such as various starches. Potato starch is one polysaccharide that may be used. Amylopectin, and more particularly, modified (cross-linked) pregelatinized amylopectin may be especially advantageous for use in a hemostatic sponge. Natural plant based polysaccharides tend to be biocompatible, bisorbable and free of animal components. While plant-based polysaccharides are preferred as hemostatic agents for the invention, gelatin and other animal-derived polysaccharides may be used without departing from the scope of the invention. Other hemostatic agents that may be used may include sephadex, debrisan, a modified starch, chitisan, and unmodified starches. While a sponge will most often contain one hemostatic agent (or have essentially one hemostatic agent where 95% or more of the hemostatic agent is one particular hemostatic agent), the invention is not so limited. Hemostatic sponges could contain more than one hemostatic agent in significant or insignificant quantities without departing from the scope of the invention.

In some embodiments where multiple hemostatic agents are used, the multiple agents may include two or more of the agents above. For example if amylopectin is used, the hemostatic agents in the mixture may be 60%, 70%, 80%, 90%, or 95% amylopectin with the remainder being amylose or some other hemostatic agent. As discussed herein, amylopectin may be advantageously employed as a hemostatic agent. While mixtures with 60% or more amylopectin or modified pregelatinized potato starch may be advantageous, other mixtures of various hemostatic agents can be employed without departing from the scope of the invention.

Sponges made according to the present invention may also include one or more binding agents. Example binding agents may include polyethylene glycol, glycerol, sorbitol, erythritol, propylene glycol, pentaerythritol, glycerol esters, hydroxypropylmethyl cellulose (HPMC), hydroxypropylcellulose (HPC), hydroxypropylethylcellulose (HPEC), xanthum gum, and guar gum. While water-soluble binding agents are preferred, binding agents soluble in other solvents could be used without departing from the scope of the invention. In addition, the invention is not limited to sponges made using a single binding agent. One or more binding agents may be used to create the sponge without departing from the scope of the invention.

In some embodiments, the sponge may include a clotting accelerator to speed the clotting process. Suitable clotting accelerators, for example, may include calcium sales such as calcium chloride, prothrombin, and vitamin K. The amount of clotting accelerator added to the sponge may depend upon the application but it may be a small percentage by weight as compared to the hemostatic agent or a larger percentage by weight of the hemostatic agent.

In some embodiments, it may also be desirable to add medications to the sponge such as antibacterials, antifungals, or polyglucans. Such medications may be mixed in with the hemostatic agent while the sponge is being made or applied to the surface of the sponge after manufacture.

The inventors have found that a sponge where the percentage by weight of binding agent is approximately one quarter to approximately equal that of the hemostatic agent can produce a sponge with desirable qualities. In some cases, the invention may produce good results where the percentage by weight of binding agent is approximately one eighth to approximately sixteen times that of the hemostatic agent A fairly flexible sponge can be made using equal ratios of HPC and modified pregelatinized potato starch. A fairly flexible sponge may also be made using a ratio by weight of one half as much binder. Such sponges will be discussed in more detail below. Sponges with other ratios of percentage by weight of the binding agent to the hemostatic agent can be made without departing from the scope of the invention.

Depending upon the type of wounds for which the sponge is intended, it may be advantageous to create the sponge so that it has sufficient flexibility that it will not crack when bent a certain amount. Embodiments of the invention may be designed such that they can bend between 0 and 45 degrees, 0 and 60 degrees, 0 and 75 degrees, 0 and 90 degrees, 0 and 105 degrees, 0 and 120 degrees, 0 and 135 degrees, 0 and 150 degrees, 0 and 165 degrees, or 0 and 180 degrees (folded over) without cracking. The sponge created using a mixture of 1% modified pregelatinized potato starch/1% HPC described below may have sufficient flexibility to be bent in half without cracking. Any degree of flexibility is within the scope of the invention but some embodiments may have substantial flexibility.

Sponges according to the invention may be made by the following process. First, one or more binding agents may be dissolved in a solvent. A water solvent is preferable but other solvents may be used without departing from the scope of the invention. The amount of binding agent used may be a percentage by weight of the solution. In a preferred embodiment, the binding agent may be approximately 0.5% by weight of the solution but other percentages by weight may be used without departing from the scope of the invention. While in this embodiment, the binding agent is first dissolved in the solvent, the binding agent and hemostatic agent could be dissolved together without departing from the scope of the invention.

Second, an amount of a hemostatic agent may be added to the solution. Any of the hemostatic agents discussed above may be used. If a clotting accelerator is being used, then it may be added at this time as well (or it may be added simultaneously with the binding agent and the hemostatic agent, simultaneously with the binding agent alone, or sequentially before or after the hemostatic agent). The amount of starch may be approximately 0.5-8% by weight of the solution. Also, the amount of starch by weight may be approximately one eighth up to approximately sixteen times as great as the amount of binding agent by weight. As discussed above, multiple hemostatic agents and binding agents may be used. In such situations, their collective weights and/or comparative ratios may be maintained as discussed above. Other percentages by weight and other comparative ratios may be used without departing from the scope of the invention.

After the solution is mixed, it may be sheared, such as, for example, by shearing in a blender. This step may be omitted without departing from the scope of the invention. Shearing may promote consistent mixing and produce a more consistent sponge. The solution may then, optionally, be degassed, particularly if bubbles are present prior to freeze drying. The solution may then be freeze dried using various conventional techniques.

While many different types of freeze drying can be used without departing from the scope of the invention, an example is to initially freeze the solution to −40 degrees Celcius. Once the product reaches that temperature, one may hold it at that temperature for an additional 2 hours. When the condenser of the freeze drying apparatus reaches a set point of −60 degrees C., the chamber should begin to evacuate. Drying may initiate when the pressure reaches 100 mTorr. The vacuum may be controlled at approximately 100 mTorr throughout the drying cycle.

During the drying cycle, the product may be held at −40 degrees Celcius for 1 hour. Then, the product may be ramped to −20 degrees Celcius over 2.5 hours. Then the product may be ramped to 0 degrees Celcius over 5 hours and held at that temperature for an additional 5 hours. Then, the product may be ramped to 20 degrees Celcius over 1 hour and held at that temperature for an additional 60 minutes.

Secondary drying may be initiated when the product probe temperature reaches 22 degrees Celcius. At this point, heat may be added to heat the product to 25 degrees Celcius for 120 minutes with vacuum set to 100 mTorr. Freezing and drying may be done in the same chamber or different chambers and any other freeze drying technique used without departing from the scope of the invention.

As an example, a sponge may be prepared using water as a solvent and creating a mixture of 2% by weight of modified pregelatinized potato starch or modified pregelatinized amylopectin and 1% to 2% by weight of HPMC. The mixture may then be freeze dried. Other examples include sponges made using mixtures with the following percentages by weight of each ingredient using water as a solvent: (a) 0.5% HPC and 2% modified pregelatinized potato starch or amylopectin, (b) 1% HPC and 2% modified pregelatinized potato starch or modified pregelatinized amylopectin, (c) 1% HPC and 2% modified pregelatinized potato starch or modified pregelatinized amylopectin, or (d) 1% HPEC and 2% modified pregelatinized potato starch or modified pregelatinized amylopectin, A sponge prepared according to the invention may be used to treat a bleeding wound. The sponge may be placed in contact with the bleeding wound to speed up and promote clotting of blood around the wound. Some or all of the sponge may dissolve in the process of treating the wound. Excess material may be removed from the wound, in most cases without damaging any clots that have formed. In applications such as bleeding gums or other oral tissue during oral surgery, application of the sponge to such wounds may rapidly stop bleeding in a convenient, easy to use manner. Sponge material may be inserted into the nose to stop nose bleeds or greatly reduce the flow of blood. While these are examples where the sponge may be particularly useful, it may be used for treating any bleeding wound without departing from the scope of the invention.

The sponge material may also be used as a wound exudate treatment. The sponge material with its hemostatic agents may be used as a skin-sloughing agent to absorb puss from a wound.

The invention also encompasses the use of amylopectin, modified pregelatinized potato starch, pregelatinized starches, or modified pregelatinized starches in various forms as a hemostatic agent. Amylopectin particles may be used in various applications as a hemostatic agent. Modified (cross-linked) pregelatinized amylopectin particles may be used as a hemostatic agent. This substance is easily absorbed by the body. It may promote stable clotting because it is a long-branch molecule. It may also promote rapid clotting due to its ability to rapidly absorb water. Particles of other pregelatinized starches or modified pregelatinized starches may also be used as hemostatic agents and may perform better than hemostatic agents that have not been pregelatinized. As was the case above in connection with the sponge, amylopectin, modified pregelatinized amylopectin, pregelatinized starches, or modified pregelatinized polysaccharides may be combined with one another or with other hemostatic agents in particle form (or in other forms as set forth below). Such a mixture could include 50%, 60%, 70%, 80%, 90%, 95% or any other percentage of amylopectin, modified pregelatinized amylopectin, pregelatinized starches or modified pregelatinized starches, with the remainder of the hemostatic powder mixture being particles of another hemostatic agent (or another one of amylopectin, modified pregelatinized amylopectin, pregelatinized starches or modified pregelatinized starches).

Where a particle form of amylopectin, modified pregelatinized amylopectin, pregelatinized starches or modified pregelatinized starches is used as a hemostatic agent, particles of a clotting accelerator such as those discussed above may be combined with the hemostatic agent in treating a wound. The same options discussed above in connection with sponge in terms of medications are applicable to the use of these agents in particle form. Particles of the medication could be mixed with the particles of hemostatic agent(s), and/or clotting accelators.

To make the amylopectin, modified pregelatinized amylopectin, amylopectin, modified pregelatinized amylopectin, pregelatinized starch or modified pregelatinized starch particles, the substance may be dissolved in a solvent and then freeze dried by any suitable freeze drying technique. In some cases, the amylopectin, modified pregelatinized amylopectin, pregelatinized starch or modified pregelatinized starch may be mixed, in a ratio by weight of 80/20, 70/30, 60/40 or any other ratio, with one another or another hemostatic agent such as amylose. It may also be mixed with multiple hemostatic agents. In some cases, a clotting agent may be dissolved and mixed with the hemostatic agents before freeze drying. The same options regarding shearing and degassing are applicable to the powder form of the hemostatic agent. The resulting particles may have an average diameter of 0.5 µm to 1,000 µm with a preferred mean diameter of 2 µm.

Persons of skill in the art will also recognize that techniques for making starch fibers may be used to make fibers of amylopectin, modified pregelatinized amylopectin. Such techniques may also be useful for making fibers of pregelatinized starch or modified pregelatinized starch. Fibers of modified pregelatinized potato starch may also be made. Such fibers may include a clotting accelerator and/or a medication in the form of one of the options above. Also, a mesh can be created containing amylopectin or modified pregelatinized amylopectin. A mesh may also be created containing a pregelatinized starch or a modified pregelatinized starch.

Whether in the form of particles, fibers, or mesh, such hemostatic material may be used to treat a bleeding wound or wound exudate. To do so, the hemostatic agent (alone or in combination with the various other substances discussed above) may be brought into contact with the wound. Where the wound is a bleeding wound, the hemostatic agent may enhance the speed of clotting. In some embodiments, it may also form robust clots.

In some embodiments, amylopectin, modified pregelatinized amylopectin, and/or modified pregelatinized potato starch may form a portion of a porous solid structure. The porous solid structure may be used to treat wounds by applying the porous solid structure to such wounds and making the porous solid structure come into contact with the wound.

An experiment was run to determine the viscosity and water absorption capabilities of an embodiment of the invention. 3 grams of particles of modified pregelatinized amylopectin with a mesh size of approximately 100 were emptied into a beaker containing 175 ml of water at approximately 90 degrees Fahrenheit. The starch was added gradually until it was visibly dissolved in the water. A viscometer was set at 60 rpm and was used to measure the viscosity of the solution at T=0 and T=20 minutes. The viscosity was 20 cps at T=0 and 66 cps at T=20 minutes. The high viscosity of this embodiment demonstrates the high water absorption capability of the invention. Thus, under the above test conditions, it is believed that the viscosity of the test solution will range between 15 and 25 cps at T=0 and 60-75 cps at T=20 minutes. A viscosity of anything greater than 30 cps at T=20 minutes under the above conditions is believed to be a substantial improvement over existing hemostatic agents.

Any of the above described hemostatic agents may be used to create a film. The film may be formed and used by itself as a hemostatic agent, or may be formed on another surface—such as the surface of a bandage. To make a film, the hemostatic agent may be dissolved in a solvent with a binder (with any of the percentages by weight discussed above). After mixing, the solvent is evaporated, leaving behind a film.

While particles of the invention may be sprinkled in a bleeding wound or sprinkled in a wound to use as a wound exudate, the hemostatic agents of the invention may also be used with bandages. The description below describes two novel arrangements for bandages that may employ hemostatic agents. While any hemostatic agent may be used with the novel bandages described below, the new hemostatic agents described above may be most advantageous.

FIG. 1 illustrates a first example embodiment of a bandage 10 with a hemostatic agent. The bandage 10 may comprise tabs 12 and wound portion 16. The wound portion will typically be placed over at least part of a wound when the bandage 10 is used. Tabs 12 may be coated with an adhesive 14 on all of or at least a portion of the underside of tabs 12. Tabs 12 and wound portion 16 may be one piece or multiple pieces. In this embodiment, they are one piece. Tabs 12 and wound portion 16 may be made of a layer of plastic. In this embodiment, bandage 12 is manufactured such that tabs 12 are inclined relative to wound portion 16.

By so manufacturing bandage 10, tabs 12 are configured such that they will be in tension with the wound portion 16 when tabs 12 are attached to the skin (or a covering over the skin) using the adhesive. Such tension may be caused because tabs 12 will tend to exert a force as they try to return to their original position. Because the tabs 12 when adhered to the skin will tend to pull up on the skin, the tension with wound portion 16 may tend to cause wound portion 16 to press down on a wound. Such positive pressure may assist in clotting blood. Positive pressure may also assist in causing a hemostatic agent to make contact with a wound.

Figure 2:
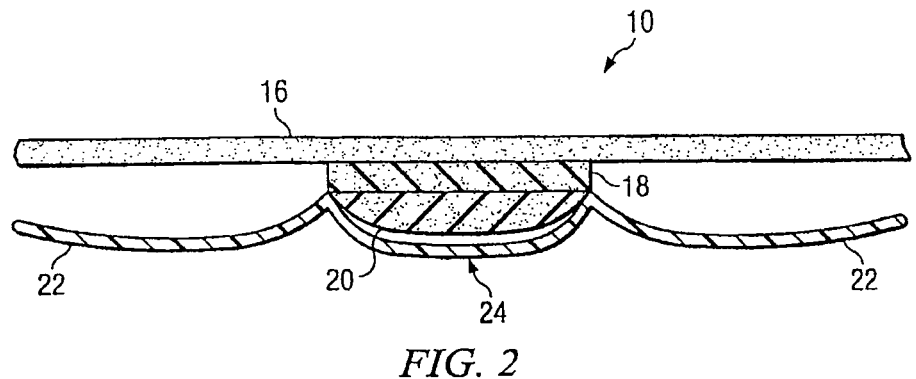
FIG. 2 illustrates a side view of the example embodiment of FIG. 1.

FIG. 2 illustrates a side view of a portion of the underside of wound portion 16 of bandage 10. As illustrated, bandage 10 comprises padded material 18, hemostatic agent 20, and removable covering 24. Each of these components is optional and may be omitted without departing from the scope of the invention. A hemostatic agent could simply be a film on the underside of wound portion 16. In this embodiment, however, additional structure is provided.

Padded material 18 may be absorbent or unabsorbent. Padded material may be adhesively attached to the underside of wound portion 16 or loosely or indirectly held in place, such as by using removable covering 24 to cover padded material 18 (not explicitly shown) around its edges. Padded material 18 may be omitted without departing from the scope of the invention. Padded material 18 may include padded materials such as are used in ordinary adhesive bandages used for small cuts on the fingers. Padded material 18 may be any other suitable padded material without departing from the scope of the invention.

Hemostatic agent 20 may comprise any of the hemostatic agents discussed above in any of the forms discussed above. Thus, for example, hemostatic agent 20 may be a polysaccharide, a starch, a pregelatinized starch, a modified pregelatinized starch, modified pregelatinized potato starch, amylopectin, potato starch, pregelatinized potato starch, pregelatinized amylopectin, or modified pregelatinized amylopectin. A combination of such hemostatic agents or a combination of these agents with other agents may be used without departing from the scope of the invention.

Hemostatic agent 20 may comprise particles, a gauze, a mesh, a sponge, fibers, a film (such as on padded material 18), or a porous solid. Hemostatic agent 20 may be directly attached to wound portion 16 with an adhesive (when padded material 18 is omitted) or indirectly attached to wound portion 16 by attachment to padded material 18 with an adhesive. More advantageously, hemostatic agent 20 may be attached to wound portion 16 directly or indirectly in a loose fashion so that when bandage 10 is removed from a wound, there is a reduced chance of a scab or other clot being torn, damaged, or pulled from the wound.

In the embodiment illustrated in FIG. 2, hemostatic agent 20 is attached to wound portion 16 using removable cover 24. Removable cover 24 may enclose hemostatic agent 20 and form a cover over it. Where padded material 18 is present, removable cover 24 may be placed over hemostatic agent and adhered to, for example, edges of hemostatic agent 20—where a sponge or film. In other embodiments, removable cover 24 may be adhered to the underside of padded material 18 and/or wound portion 16 of bandage 10. In addition to adhesive connections, removable cover 24 could be fixed by a friction fit in a slot or using some other mechanism to create a compartment for hemostatic agent 20.

In this embodiment, removable cover 24 comprises tabs 22. While this embodiment has two tabs 22, other embodiments may have one tab or more than two tabs. Tabs 22 may be used to remove removable cover 24 after bandage 10 has been affixed to a wound—thus exposing the wound to hemostatic agent 20. In some embodiments, removable cover 24 may have a perforation such that it tears when tabs 22 are pulled. In some embodiments, a portion of wound portion 16, or padded material 18 (when present), may be recessed so as to better hold hemostatic agent 20 in place during the removal of removable cover 24. Neither portion is required to be recessed, however. Removable cover 24 should be configured such that it does not cause hemostatic agent 20 to be completely removed from the wound when removable cover 24 is being removed.

Figure 3:
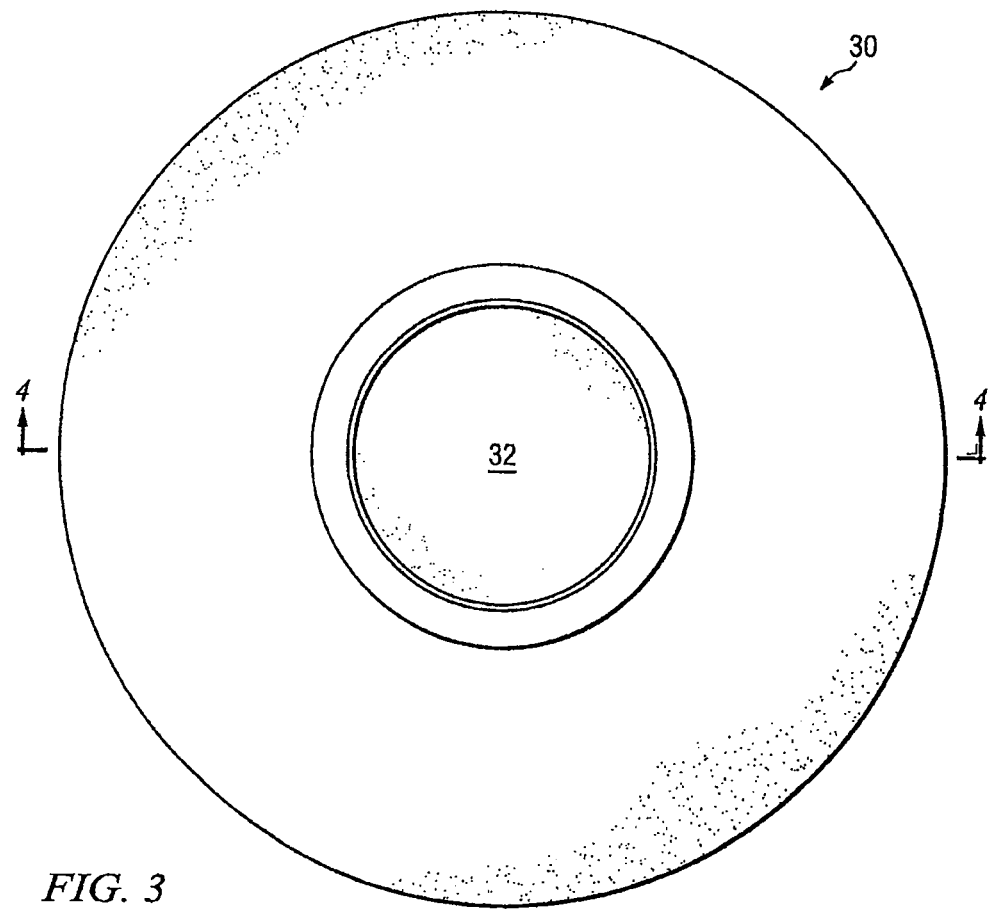
FIG. 3 illustrates a second example embodiment of a bandage with a hemostatic agent in accordance with one aspect of the invention.

FIG. 3 illustrates a second example embodiment of a bandage 30 with a hemostatic agent in accordance with one aspect of the invention. Bandage 30 comprises plunger 32 which may be depressed to apply pressure to a wound. In some embodiments, plunger 32 may latch into position—either to remain in that position or to be released if the embodiment permits release of the plunger. In other embodiments, plunger 32 may be held down manually and may move back into its original position or close to its original position when released. Bandage 30 may include an adhesive on the underside of bandage 30 outside of the area of plunger 32. The adhesive may cover all or part of this area.

In an alternative embodiment, plunger 32 may be replaced simply by a padded material and a hemostatic agent, or a hemostatic agent alone on the underside of bandage 30. A removable cover may be used to cover the hemostatic agent in such an embodiment. Any of the options discussed above for the type of hemostatic agent (e.g. modified pregelatinized amylopectin) and the form of the hemostatic agent (e.g. particles, sponge, etc) are applicable to such an embodiment. Any of the options discussed above in connection with FIG. 1 may be used to keep the hemostatic agent attached to bandage 30 either directly or indirectly.

Figure 4:
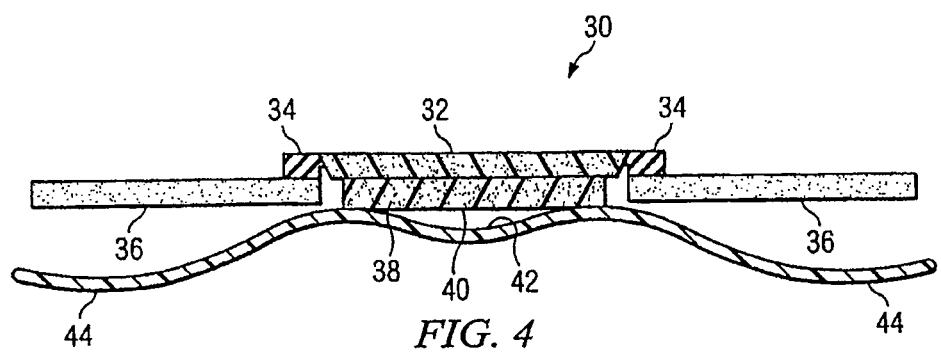
FIG. 4 illustrates a side view of the example embodiment of FIG. 3 before a plunger has been depressed.

FIG. 4 illustrates a side view of bandage 30 to illustrate the plunger 32 prior to being depressed in one embodiment of the invention. Plunger tabs 34 may be frangibly connected to plunger 32 or simply connected to an adhesive pad portion of bandage 30. In the example embodiment illustrated, an adhesive 36 is on the underside of a portion of bandage 30. The adhesive may cover all or a portion of the underside of bandage 30 and may be used to affix bandage 30 to the skin or a covering of the skin.

Bandage 30 may further comprise padded material 38, hemostatic agent 40, and removable cover 42 with tabs 44. All of the options discussed above in connection with FIGS. 1-2 are equally applicable here for padded material 38, hemostatic agent 40, and removable cover 42. Some or all of these elements may be omitted and other elements added without departing from the scope of the invention. These elements may be configured in an identical or similar manner to the configuration discussed above in connection with FIGS. 1-2. Here, plunger tabs 34 may extend below the surface of bandage 30 (not explicitly shown) to create a recess for padded material 38, hemostatic material 40, or both. All of the options to create a recess discussed above are equally applicable and a recess could be omitted without departing from the scope of the invention. All options for the type and form of hemostatic agent discussed herein are options for hemostatic agent 40.

Figure 5:
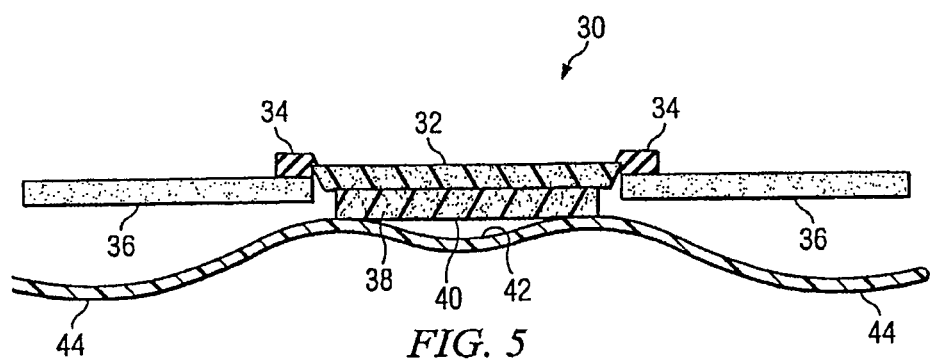
FIG. 5 illustrates a side view of the example embodiment of FIG. 3 after a plunger has been depressed.

FIG. 5 illustrates plunger 32 in its depressed position. In this embodiment, plunger 32 is latched in position by plunger tabs 34. As discussed above, in some embodiments, plunger 32 may be released from plunger tabs 34 while in other embodiments it will remain depressed. In other embodiments, plunger 32 may not latch down and may be held down manually.

The various embodiments discussed in connection with FIGS. 3-5 may be especially advantageous for use in applications where a catheter is used. Such catheters may result in a fairly deep wound and the embodiments of the invention set forth may serve to enhance clotting of such a wound.

In operation, any of the embodiments discussed in connection with FIGS. 1-5 may be adhesively attached to the skin (or a covering on the skin) adjacent a wound. Once the bandage is adhered or partially adhered, all or a portion of the removable cover may be removed to expose the wound to a hemostatic agent.

Although the present invention has been described in detail, it should be understood that various changes, substitutions and alterations can be made hereto without departing from the sphere and scope of the invention as defined by the appended claims.

To aid the Patent Office and any readers of any patent issued on this application and interpreting the claims appended hereto, Applicants wish to note that they do not intend any of the appended claims to invoke Paragraph 6 of 35 U.S.C. §112 as it exists on the date of filing hereof unless "means for" or "step for" are used in the particular claim.

What is claimed is:

1. A method of treating a wound to clot blood comprising:
applying particles of a non-porous pregelatinized potato starch to a bleeding wound.

2. The method of claim 1, wherein the particles of the non-porous pregelatinized potato starch have an average diameter of 0.5 μm to 1,000 μm.

3. The method of claim 1, further comprising applying particles of a clotting accelerator to the bleeding wound.

4. The method of claim 3, wherein the clotting accelerator is selected from one of calcium chloride, prothrombin, and vitamin K.

5. The method of claim 3, wherein the particles of the non-porous pregelatinized potato starch and the particles of the clotting accelerator have an average diameter of 0.5 μm to 1,000 μm.

6. The method of claim 1, further comprising applying particles of a medication to the bleeding wound.

7. The method of claim 6, wherein the medication is selected from one of an antibacterial, an antifungal, and a polyglucan.

8. The method of claim 6, wherein the particles of the non-porous pregelatinized potato starch and the particles of the medication have an average diameter of 0.5 μm to 1,000 μm.

9. The method of claim 1, further comprising:
applying particles of a clotting accelerator to the bleeding wound; and
applying particles of a medication to the bleeding wound.

10. The method of claim 1, further comprising applying particles of one or more additional hemostatic agents to the bleeding wound.

11. A method of claim 1, wherein the applying the particles of the non-porous pregelatinized potato starch to the bleeding wound comprises sprinkling the particles of the non-porous pregelatinized potato starch into the bleeding wound.

12. The method of claim 1, wherein the applying the particles of the non-porous pregelatinized potato starch to the bleeding wound comprises applying the particles of the non-porous pregelatinized potato starch to the wound using a bandage, the particles of the non-porous pregelatinized potato starch being directly attached to a wound portion of the bandage using an adhesive.

13. The method of claim 1, wherein the applying the particles of the non-porous pregelatinized potato starch to the bleeding wound comprises applying the particles of the non-porous pregelatinized potato starch to the wound using a bandage, the particles of the non-porous pregelatinized potato starch being indirectly attached to a wound portion of the bandage using an adhesive and a padded material.

* * * * *